United States Patent [19]

Morris

[11] 4,169,472
[45] Oct. 2, 1979

[54] SURGICAL DRAPE

[75] Inventor: Henrietta K. Morris, Old Bridge, N.J.

[73] Assignee: Johnson & Johnson, New Brunswick, N.J.

[21] Appl. No.: 896,838

[22] Filed: Apr. 17, 1978

[51] Int. Cl.² ............................................. A61B 19/06
[52] U.S. Cl. ............................................... 128/132 D
[58] Field of Search ............... 128/132 R, 132 D, 275, 128/283, 286, 287, 292; 2/49 R, 49 A

[56] References Cited

U.S. PATENT DOCUMENTS

| | | | |
|---|---|---|---|
| 3,364,928 | 1/1968 | Creager, Jr. et al. | 128/132 D |
| 3,452,750 | 7/1969 | Blanford | 128/132 D |
| 3,791,382 | 2/1974 | Collins | 128/132 D |
| 3,882,859 | 5/1975 | Ericson | 128/132 D |
| 3,945,048 | 3/1976 | Shearer | 2/49 R |
| 4,089,331 | 5/1978 | Hartigan et al. | 128/132 D |

Primary Examiner—Robert W. Michell
Assistant Examiner—C. F. Rosenbaum

[57] ABSTRACT

A surgical drape comprising a main sheet, a liquid impervious bag for collecting liquids such as blood and saline, and means for channeling liquids into the bag for storage. In a preferred embodiment the bag also includes a liquid pervious retainer means for holding articles such as sponges which are to be counted when the surgical procedure is finished. Optionally, the drape may have a reinforcing panel or a fenestration or both. The fenestration may be covered with a closure means, such as a thin film, which carries adhesive on its bottom surface.

18 Claims, 15 Drawing Figures

U.S. Patent  Oct. 2, 1979  Sheet 1 of 5  4,169,472
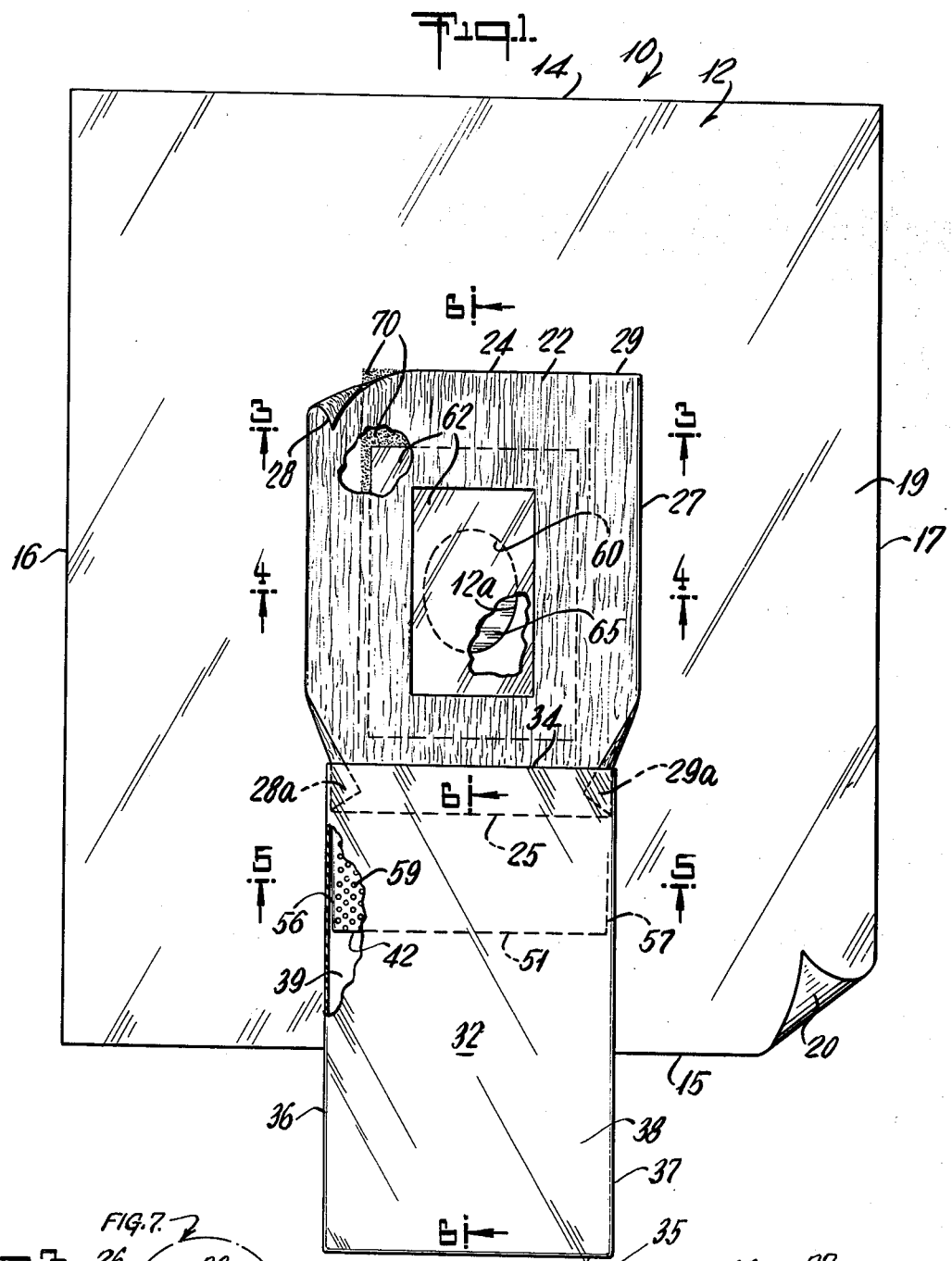

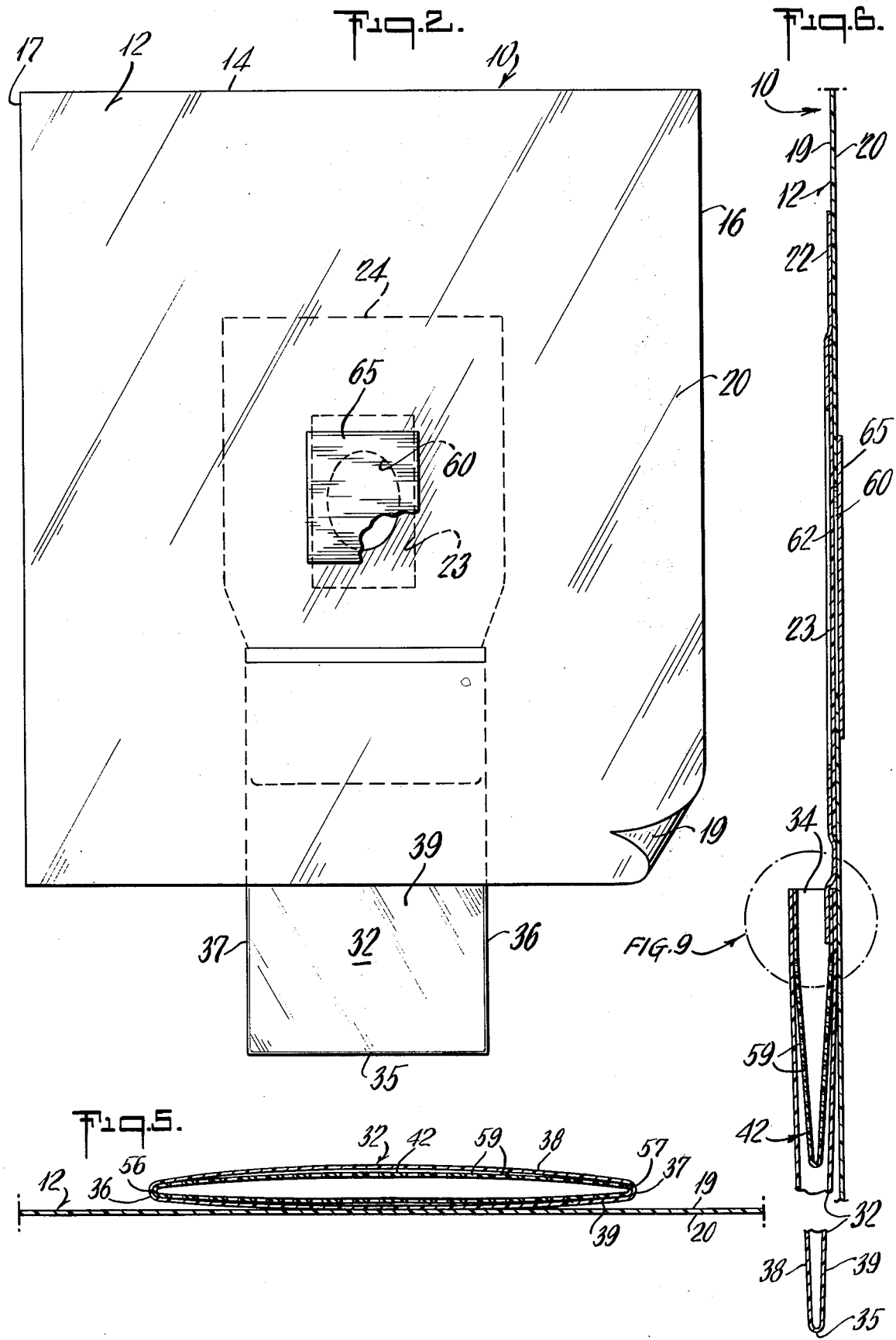

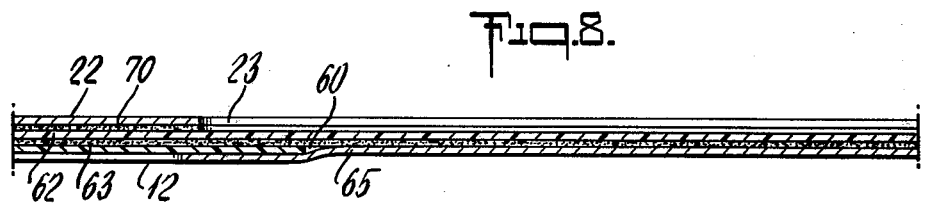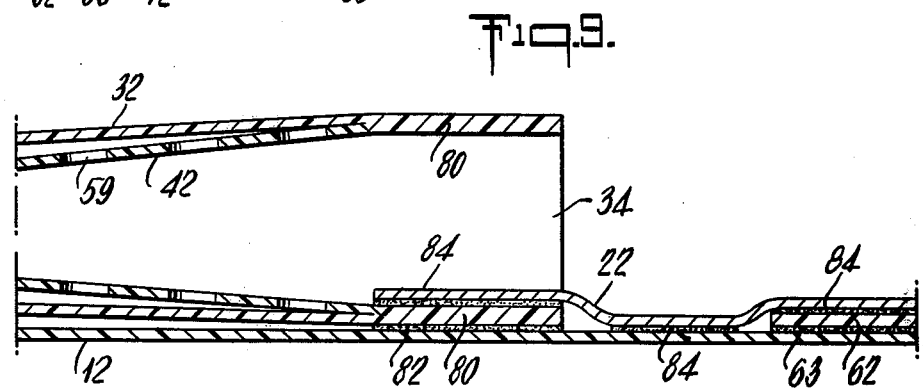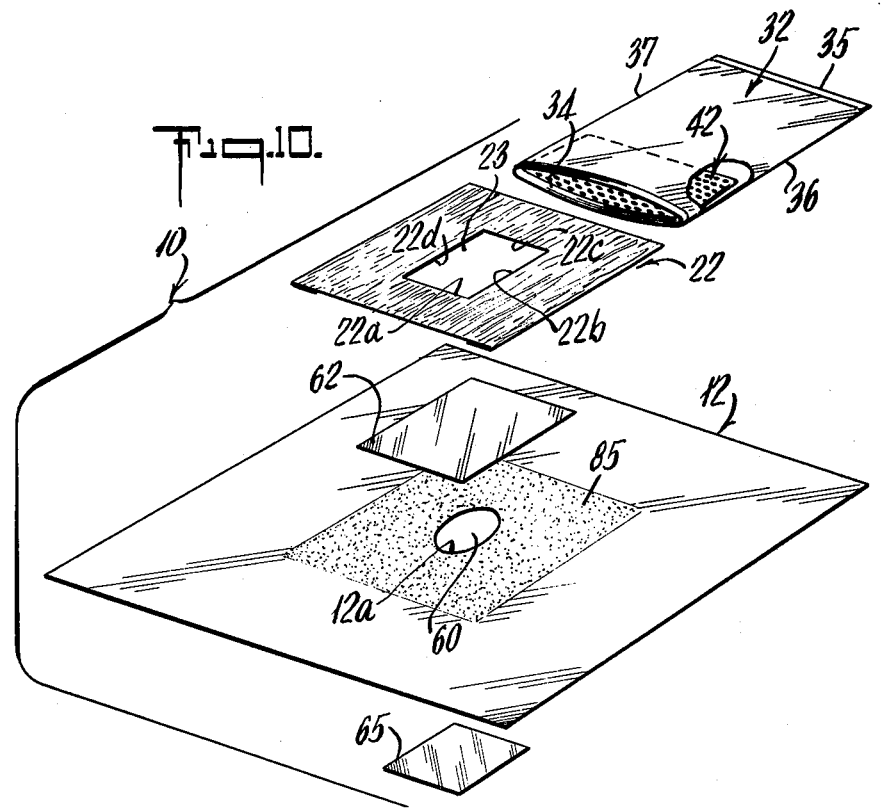

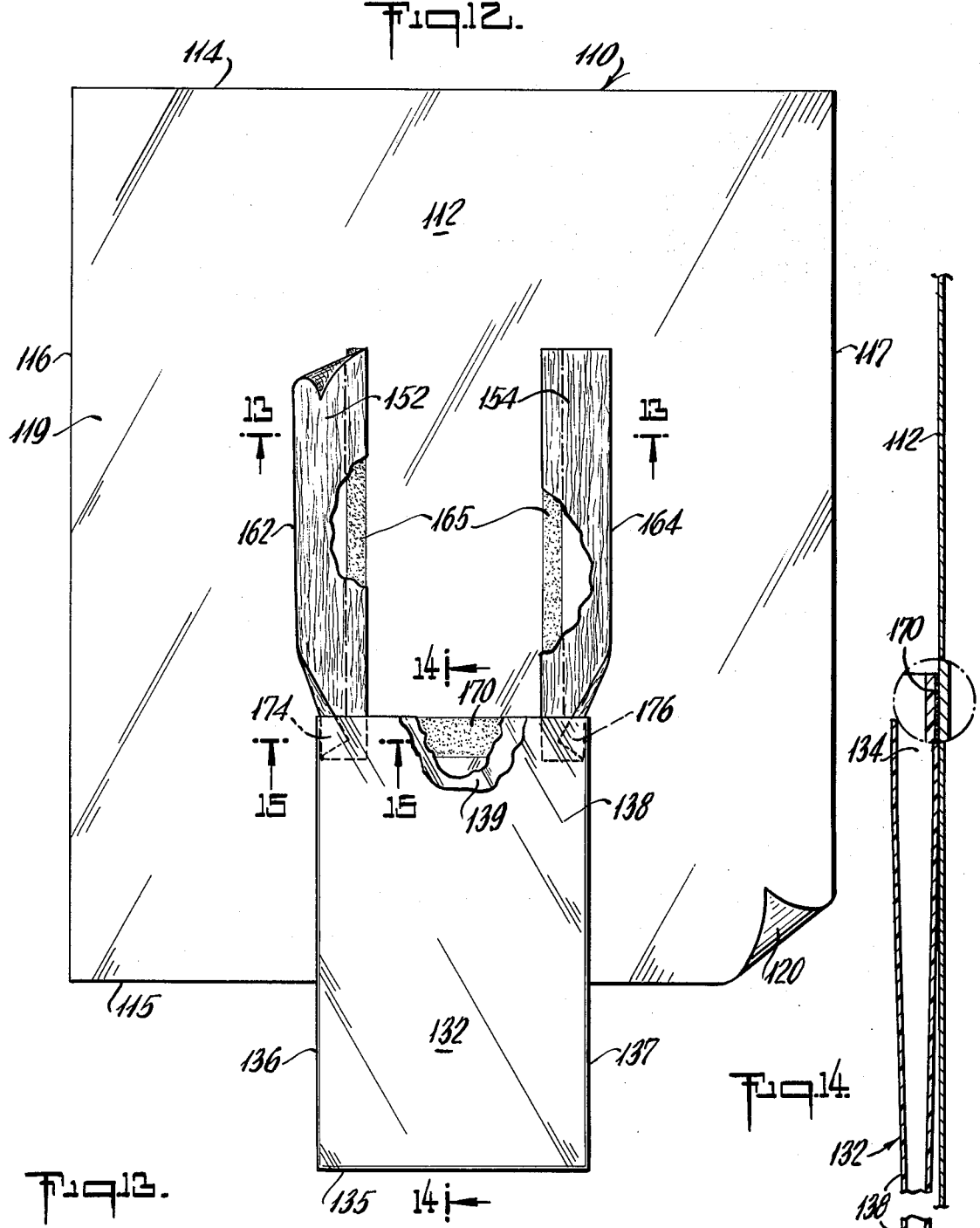
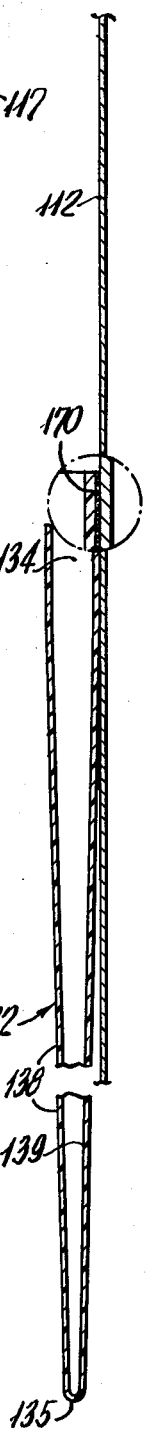
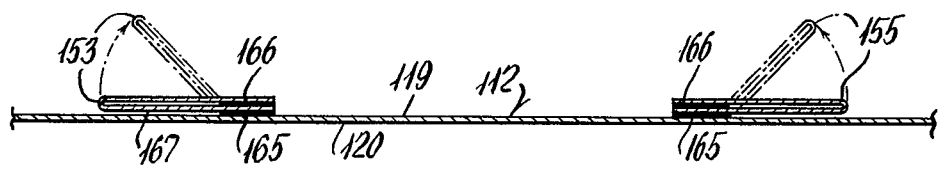
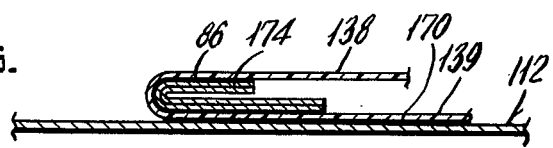

SURGICAL DRAPE

TECHNICAL FIELD

This invention relates to surgical drapes, especially those which are disposable, and more particularly, to disposable surgical drapes which are suitable for use in surgical procedures involving the patient's head.

BACKGROUND ART

A patient is typically prepared for surgery involving the head in the following manner. The patient is positioned on the operating table and a Mayo neuro-surgical table is positioned over the patient, leaving his head and neck uncovered. The head is shaved (either partially or completely) and scrubbed with, e.g. hexachlorophene solution. A clean towel is placed under the head and the line of incision is marked on the scalp. Some surgeons prefer at this point to apply a single layer of gauze over the patients's head. This serves to confine any loose hair which might find its way into the operative field when the patient's scalp has only been partially shaved. Four or more towels are placed around the operative site and are secured with towel clamps or sutures. A sterile conductive sheet is placed over the neurosurgical table so that one edge reaches up to the line of incision. This sheet is secured to the nearest towel with Michel clips. A craniotomy sheet, with its fenestration placed over the operative site, is placed over the entire field and secured with Michel clips. Half sheets are used for additional draping, and sufficient slack is left in the various drapes to permit operating table adjustments. The desired surgical instruments and auxiliary equipment, e.g., sponges, basins, and irrigating solutions, are placed on the overhead or neurosurgical table. A typical craniotomy sheet is fenestrated near its center and has a slit running from the edge of the fenestration to an outer edge of the drape. The slit forms what might be considered two wings of fabric; after the craniotomy sheet is positioned on the patient, these wings may be adjusted and secured together over a bucket (commonly called a "kick pail") so that irrigating fluids and blood drip into the kick pail rather than on the floor.

Information (including that given above) respecting the preparation and draping of a patient for surgery involving the head may be found in the following references: *Alexander's Care of the Patient in Surgery*, 5th Edition, C.V. Mosby Company, St. Louis, Missouri (1972); Aseptic Treatment of Wounds, The Macmillan Company, New York, New York (1954); and Operating Room Technique, 2nd Edition, The C. V. Mosby Company (1949).

Inasmuch as the above described draping procedure involves a large number of drapes and the use of securing means such as towel clamps, sutures, or knots made in, or with, fabric, a substantial amount of valuable operating room time is spent in draping and otherwise preparing the patient for surgery. In addition, the use of the wing-like portions of the fenestrated, slit craniotomy sheet to direct liquids into the kick pail does not insure that all such liquid will reach that container. The presence of the kick pail at or near the feet of the surgeon and his assistants is inconvenient and the pail is subject to being inadvertently knocked over.

DISCLOSURE OF THE INVENTION

In accordance with the present invention, there is provided a surgical drape which is particularly suited for a variety of surgical procedures involving the head. The drape may be easily and quickly applied to the patient and reduces the number of towels and drapes heretofore used. The drape includes bag means for collecting fluids, thus eliminating the need for a kick pail. The drape also includes means for channeling and directing liquids, such as blood and irrigating solutions, from the operative site into the collection bag. The drape may be easily and quickly made from readily available, inexpensive materials and thus may be discarded after use.

In accordance with one aspect of the present invention, there is provided a surgical drape comprising a main sheet of generally flexible drapable material, a liquid impervious bag means, and a pair of spaced apart strips of material; said main sheet comprising an upper surface, a lower surface, a bottom edge and a pair of opposed side edges; said bag means comprising a front cover sheet, a back cover sheet, an open end and a closed end and being secured to the upper surface of said main sheet; said strips of material being secured to the upper surface of said main sheet and having flap portions which are free of attachment to said main sheet, the respective bottom ends of said strips of material being located in the open end of said bag means, the lower surface of the bottom ends of said flap portions being secured to the lower surface of the front cover sheet of said bag means, whereby, when said drape is in use, said flap portions may be raised at an angle to the upper surface of said main sheet to provide means for channeling liquids into said bag for storage.

In accordance with another aspect of the present invention, there is provided a surgical drape comprising a main sheet of generally flexible drapable material, a reinforcing panel, and a liquid impervious bag means; said main sheet comprising an upper surface, a lower surface, a bottom edge and a pair of opposed side edges; said reinforcing panel being secured to the upper surface of said main sheet; said reinforcing panel comprising a top edge, a bottom edge, a pair of opposed side edges, and flap portions adjacent each of its side edges; said flap portions having respective bottom ends and being free of attachment to said main sheet; said bag means comprising a front cover sheet, a back cover sheet, an open end and a closed end; said bag means being secured to the upper surface of said main sheet along a line of attachment which is generally parallel to the bottom edge of said main sheet; the respective bottom ends of said flap portions being located in the open end of said bag means, the lower surface of the bottom ends of said flap portions being secured to the lower surface of the front cover sheet of said bag means, whereby, when said drape is in use, said flap portions may be raised at an angle to the upper surface of said main sheet to provide means for channeling liquids into said bag for storage.

In accordance with still another aspect of the invention there is provided a surgical drape comprising a main sheet of generally flexible drapable material, a reinforcing panel, a fenestration, and a liquid impervious bag means; said main sheet comprising an upper surface, a lower surface, a bottom edge and a pair of opposed side edges; said main sheet having a fenestration located inwardly of the perimeter of said main sheet; said reinforcing panel being secured to the upper surface of said main sheet in the regions adjacent said fenestration; said reinforcing panel comprising a top edge, a bottom edge, a pair of opposed side edges, and flap portions adjacent each of its side edges; said flap portions having respective bottom ends and being free of attachment to said main sheet; said bag means comprising a front cover sheet, a back cover sheet, an open end and a closed end; said bag means being secured to the upper surface of said main sheet along a line of attachment which is generally parallel to the bottom edge of said main sheet; the respective bottom ends of said flap portions being located in the open end of said bag means, the lower surface of the bottom ends of said flap portions being secured to the lower surface of the front cover sheet of said bag means, whereby, when said drape is in use, said flap portions may be raised at an angle to the upper surface of said main sheet to provide means for channeling liquids into said bag for storage.

In accordance with yet another aspect of the present invention, the bag means may include a liquid pervious retainer means, preferably located a substantial distance from the bottom end of the bag means, for the collection and temporary storage of e.g., surgical sponges which can be conveniently counted after the surgical procedure has been completed.

In those embodiments of the present invention in which the drape comprises a fenestration, the latter may be covered with a closure member. This closure member preferably comprises a thin, at least translucent piece of plastic film whose bottom surface may be covered with a pressure sensitive adhesive, the latter being protected, prior to use of the drape, with a releasably adhered protective sheet.

BRIEF DESCRIPTION OF THE DRAWINGS

The invention will be better understood by referring to the appended drawings in which:

FIG. 1 is a top plan view, with some portions turned up and other portions cut away, of one embodiment of a surgical drape in accordance with the present invention;

FIG. 2 is a bottom plan view, with some portions turned up and other portions cut away, of the drape of FIG. 1;

FIG. 3 is an enlarged cross-section taken along line 3—3 of FIG. 1;

FIG. 4 is an enlarged cross-section taken along line 4—4 of FIG. 1;

FIG. 5 is an enlarged cross-section taken along line 5—5 of FIG. 1;

FIG. 6 is an enlarged cross-section taken along line 6—6 of FIG. 1;

FIG. 7 is a magnified view of the circled portion of FIG. 3;

FIG. 8 is a magnified view of the circled portion of FIG. 4;

FIG. 9 is a magnified view of the circled portion of FIG. 6;

FIG. 10 is an exploded perspective of the drape of FIG. 1;

FIG. 12 is a top plan view, with some portions turned up and other portions cut away, of a second embodiment of a surgical drape in accordance with the present invention;

FIG. 13 is an enlarged cross-section taken along line 13—13 of FIG. 12;

FIG. 14 is an enlarged cross-section, with portions magnified, taken along line 14—14 of FIG. 12; and FIG. 15 is an enlarged cross-section taken along line 15—15 of FIG. 12.

BEST MODE FOR CARRYING OUT THE INVENTION

Figure 11:
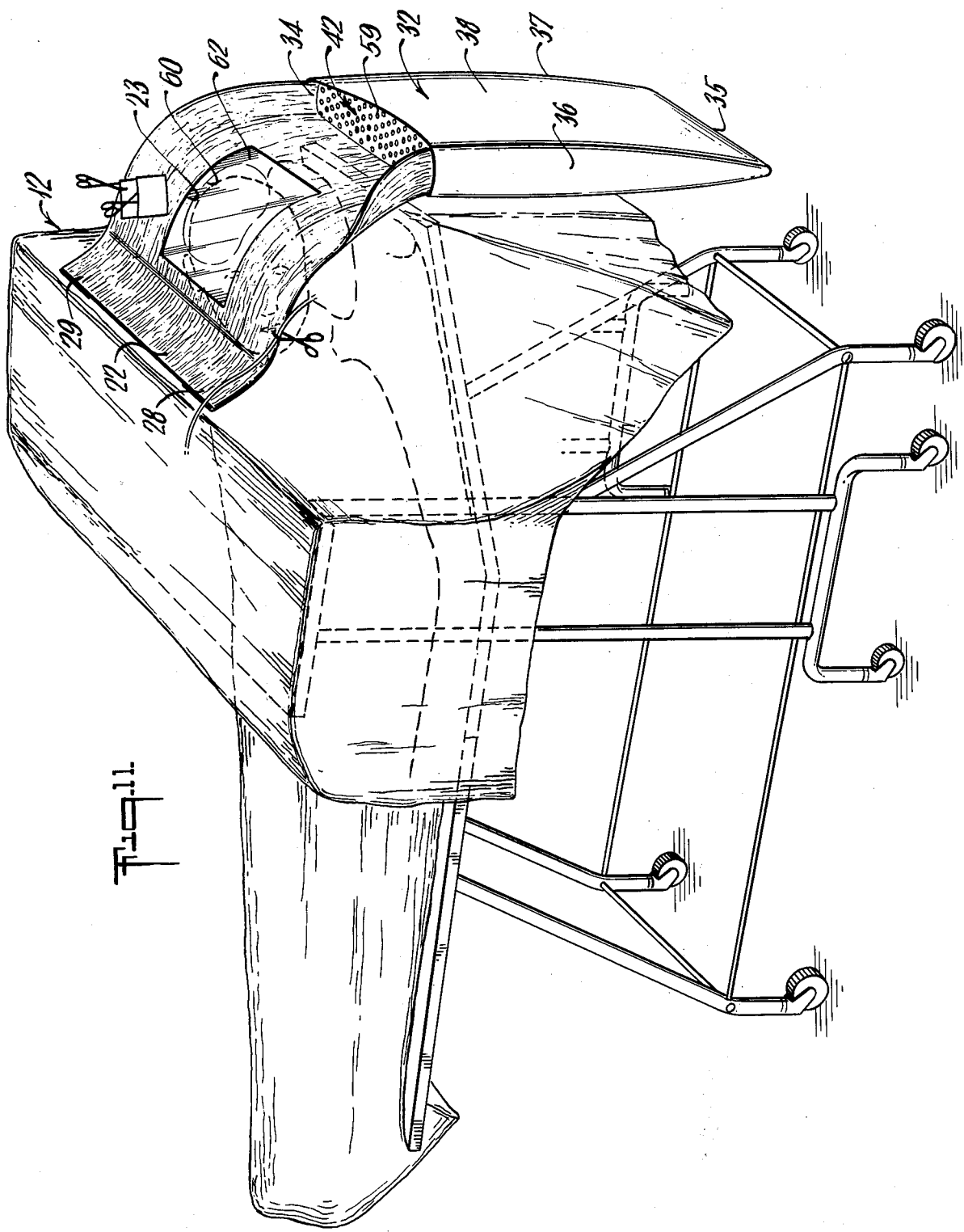
FIG. 11 is a perspective showing the drape of FIG. 1 placed over a patient about to undergo surgery.

Referring now to the drawings, and especially FIGS. 12–15, there is shown one embodiment of a surgical drape in accordance with the present invention. Drape 110 comprises a main sheet 112, a liquid impervious bag means 132, and a pair of relatively narrow, elongated strips 152, 154 of material which may comprise e.g., a nonwoven fabric or, preferably, a material which consists of a nonwoven fabric laminated to a film of plastic such as polyethylene.

Main sheet 112 comprises a generally flexible drapable material having a top edge 114, a bottom edge 115, a pair of opposed side edges 116 and 117, an upper surface 119 and a lower surface 120. The main sheet is preferably made of a relatively thin (for example, 2–5 mils) sheet of synthetic plastic material such as polyethylene, polyvinyl chloride or the like. Other well-known materials of construction, e.g., a woven fabric, a nonwoven fabric or a scrim reinforced tissue may also be used. These latter materials, if desired, may be treated according to well-known techniques to render them resistant to liquids such as water, blood, saline, alcohol and the like. Main sheet 112 may vary in size and illustratively may be 60 inches (152.4 cm.) to 80 inches (203.2 cm.) long by 60 inches (152.4 cm.) to 80 inches (203.2 cm.) wide.

In accordance with the teachings of the present invention, surgical drape 110 comprises elongated, longitudinally extending, spaced apart strips of material 152 and 154 which are secured to the upper surface of main sheet 112 inwardly of its side edges 116 and 117. As best seen in FIG. 13, strips 152 and 154 have flap portions 153 and 155, respectively, which are free of attachment to main sheet 112. Prior to use of the drape, flaps 153 and 155 lie more or less flat against the upper surface of the main sheet as seen generally in FIG. 13. During the use of the drape, as will be explained more fully hereinafter, these flaps may be raised upwardly (as illustrated in phantom in FIG. 13) to a position which is at an angle to the upper surface of main sheet 112.

As illustrated in FIG. 13, flaps 153 and 155 may consist of a double ply of material, the two plies being secured back-to-back with a suitable adhesive 166. As seen in FIG. 13, where each flap 153 and 155 has an adhesive free region 167, adhesive 166 need be applied only in sufficient quantity to hold the two plies in place. Strips 152 and 154 are preferably secured to the upper surface of the main sheet with adhesive 165 running lengthwise thereof, although in appropriate cases, other means, such as heat sealing, could also be used.

Surgical drape 110 further comprises a bag means 132 for storing liquids used in or encountered during a surgical procedure. Such bag means must be made of a material which is substantially liquid impervious. Although the bag means may comprise a woven or nonwoven fabric which has been suitably treated according to known techniques to render it liquid impervious, it is preferred that the bag means comprise a sheet of synthetic plastic material having a thickness of from about 2 mils to about 5 mils. In the preferred embodiment, both main sheet 112 and bag means 132 comprise polyethylene although other suitable synthetic plastic materials could also be used. Where plastic is used, the same is preferably treated with a suitable antistatic agent.

As can best be seen in FIGS. 12 and 14, bag means 132 is generally rectangular and comprises a first or front cover sheet 138, a second or back cover sheet 139, an open end 134, a closed end 135, and side edges 136, 137. Bag means 132 can be conveniently formed from a single sheet of plastic material by folding the sheet in half upon itself to form front cover sheet 138, back cover sheet 139, and closed end 135. The side edges of the thus folded sheet of material are sealed together, preferably by heat sealing, to form side edges 136, 137 of the bag means. The bag is secured to the upper surface of the main sheet along line of attachment 170 (FIG. 14) which runs from side to side of the bag and just below open end 134. When main sheet 112 and bag 132 comprise thermoplastic sheets, the bag may be secured to the main sheet by heat sealing; alternatively any suitable adhesive may be used.

In constructing the drape, bag means 132 is first secured to main sheet 112 along line of attachment 170 generally parallel to, and at the desired distance from, bottom edge 115 of the main sheet. Strips of material 152 and 154 are then secured to the main sheet with adhesive 165, care being taken to leave flap portions 153 and 155 free of attachment ot the main sheet. Strips 152, 154 are arranged so that their outermost longitudinal edges 162, 164 lie somewhat outside (extended) side edges 136, 137, respectively, of bag 132 and so that their bottom ends extend a short distance into open end 134 of the bag. As seen in FIG. 12, the unattached bottom ends of flap portions 153, 155 are bent over upon themselves at an angle to form bent-over bottom ends 174, 176 of flap portions 153, 155. The original lower surfaces of the bent-over bottom ends are then secured, e.g., with any suitable adhesive, to the lower surface of the front cover sheet 138 of bag means 132. Such attachment prevents the bent-over bottom ends from accidentally slipping out of bag means 132 and also tends to keep the mouth of the bag widely open for reception of liquid run-off when, during use, flap portions 153, 155 are raised into their upwardly extending position illustrated in phantom in FIG. 13.

Referring now to FIGS. 1, 2, and 10 of the drawings, there is shown a second embodiment of a surgical drape in accordance with the present invention. Drape 10 comprises a main sheet 12 having a generally inwardly located fenestration 60, a reinforcing panel 22, a liquid impervious bag means 32, a liquid pervious retainer means 42 secured to the inside of said bag means, adhesive coated closure means 62 covering said fenestration, and a removably adhered release sheet 65 covering the exposed adhesive on said closure means.

Main sheet 12 comprises a generally flexible drapable material having a top edge 14, a bottom edge 15, a pair of opposed side edges 16 and 17, an upper surface 19 and a lower surface 20. The main sheet preferably comprises a 2.5 mil sheet of polyethylene which has been rendered antistatic according to well known techniques.

Main sheet 12 has a fenestration 60 defined at least in part by an inner edge 12a of the main sheet. This fenestration, through which a surgeon will perform the operative procedure, may have any desired shape such as oval, circular, square, rectangular, diamond, etc. The drape in its preferred embodiment has a more or less oval fenestration which is located inwardly of the perimetric edges of the main sheet. The size of the fenestration may be varied; and an oval fenestration having a length of about 8-½" and a width of about 6-½" has been found suitable.

Fenestration 60 is covered on the upper surface of the drape by closure means 62 which comprises a transparent or translucent sheet or "patch" of polyvinyl chloride or similar material having a thickness of from about 1 mil to about 3 mils. This closure means is sometimes referred to in the surgical drape art as an "incise film" because, if such a closure means is employed in the surgical drape, the surgeon will make his incision directly through said closure means. Closure means 62 is sufficient in size to completely cover fenestration 60 in the main sheet. On the lower surface of the drape, within the area defined by the periphery of the fenestration, closure means 62 carries a layer of pressure sensitive adhesive 63 which, prior to the time the drape is used, is protected by a releasably adhered protective sheet 65 made from e.g., paper treated with a silicone release resin. Closure means 62 is easily secured over the fenestration by coating it with pressure sensitive adhesive 63, placing it over fenestration 60, and then pressing the adhesive coated "patch" into contact with the region of main sheet 12 lying immediately adjacent the fenestration. Protective sheet 65 is then pressed into contact with that portion of the pressure sensitive adhesive on the bottom of closure means 62 which lies within the periphery of fenestration 60.

Drape 10 further comprises a reinforcing panel 22 secured to the upper surface of main sheet 12. This reinforcing panel may comprise one or more layers of the same material used for main sheet 12. Preferably, however, the reinforcing panel has an absorbent upper surface and liquid impervious lower surface. Most preferably, the reinforcing panel consists of a sheet of liquid absorbent nonwoven fabric which has been secured, for example, by extrusion lamination techniques, adhesive, or heat sealing, to a sheet of liquids impervious plastic such as polyethylene, polypropylene, poly (ethylene terepthalate) or the like. In the preferred embodiment, the reinforcing panel is generally rectangular in shape, is smaller than main sheet 12, and comprises a top edge 24, a bottom edge 25 and a pair of opposed side edges 26, 27. As seen in FIG. 10, the reinforcing panel has interior edges 22a, 22b, 22c and 22d which define opening 23 therein. Opening 23 in the reinforcing panel may be sized so that it is smaller than, equal to, or larger than fenestration 60 in main sheet 12. Preferably, as may be seen in FIGS. 1 and 4, opening 23 is somewhat larger than fenestration 60, in which case the area of main sheet 12 surrounding fenestration 60 lies within opening 23 of the reinforcing panel in the completely assembled drape. In certain instances, it may be desirable to have the edges of opening 23 be in registry with the edges of fenestration 60 or it may be desired that opening 23 be smaller than fenestration 60. In the latter event, it will be understood that opening 23 cannot be made so much smaller than fenestration 60 that the latter is greatly reduced in size or covered over.

In accordance with the teachings of the present invention, and as can best be seen in FIGS. 3 and 4, reinforcing panel 22 comprises longitudinally extending flap portions 28 and 29 adjacent side edges 26 and 27 respectively. These flap portions are free of attachment to main sheet 12. Prior to use of the drape, flaps 28, 29 lie more or less flat against the upper surface of the main sheet as seen generally in FIG. 1. During use of the drape, these flaps may be raised upwardly (in the direction illustrated by Arrows A and B in FIG. 4) to a position which is at an angle to the upper surface of main sheet 12. Referring to FIGS. 3 and 4, it will be noticed that flaps 28 and 29 preferably consist of a double thickness of the material used for the reinforcing panel. The two layers of material which form the flaps may be held together by any suitable adhesive 70 (see FIG. 7). An adhesive 70 may also be used to secure reinforcing panel 22 to main sheet 12.

Surgical drape 10 further comprises a bag means 32 whose function is to store liquids used in or encountered during a surgical procedure. Such bag means must be made of material which is substantially liquid impervious. Although the bag means may in some cases comprise a woven or nonwoven fabric which has been suitably treated to render it liquid impervious, it is preferred that the bag means comprise a synthetic plastic material. In the embodiment under discussion, both main sheet 22 and bag means 32 comprise polyethylene.

Bag means 32 is generally rectangular and comprises a first or front cover sheet 38, a second or back cover sheet 39, an open end 34, a closed end 35, and side edge 36, 37. Bag means 32 can be formed in the same manner, discussed earlier herein, as bag means 132 or by any other suitable method.

In accordance with another aspect of the present invention, a liquid pervious retainer means 42 is provided within bag 32 for holding items, such as surgical sponges, which are counted at the end of the surgical procedure. Retainer means 42 has a bag-like structure and comprises a closed end 51 and open end 52, a pair of opposed side edges 56 and 57, and openings 59. Retainer means 42 is not as long as bag means 32 and its width is preferably just a little less than that of bag means 32. The liquid pervious material from which retainer means 42 is made may be, for example, cotton gauze or a small mesh plastic netting. Preferably however, retainer means 42 comprises a bag of synthetic plastic material having perforations near the bottom portion thereof. Retainer means 42 is conveniently and quickly made from a section of plastic material in tubular form. The length of the tubular piece of material should be the same as that desired for the retainer means while the diameter of the tubing should preferably be just slightly less than the width of bag means 32. The tubular piece of plastic material having the desired length and width is flattened to form side edges 56 and 57. One end of the flattened tubing is then sealed, preferably by heat sealing, to form closed end 51. Openings 59, conveniently ¼" in diameter, are thereafter easily provided by punching the lower portion of the retainer means with a suitable die. The openings may assume any convenient size so long as the resulting retainer means functions to hold items, such as sponges and the like and readily allow liquids to pass through into the bottom regions of bag 32. Retainer means 42 should be secured to the inside of bag 32 and near its open end, in such fashion that the items which are to be retained thereby cannot accidentally slip to the bottom of bag 32. It is preferred to secure the outer surface of retainer means 42 to the inner surface of bag 32 in a continuous, narrow band using an adhesive or heat sealing.

Referring again to FIG. 1, the unattached bottom ends of flap portions 28 and 29 are bent over upon themselves at an angle to form bent-over bottom ends 28a and 29a, respectively. The original lower surfaces of the bent-over bottom ends are secured, most conveniently with an adhesive, to the lower surface of the front cover sheet of retainer means 42 to provide a structural arrangement analogous to that obtained when bent-over bottom ends 174, 176 in drape 110 are attached to the lower surface of the front cover sheet 138 of bag means 132.

Drape 10 of the present invention may be easily and quickly assembled in the manner described below. The dimensions stated in connection with the following description are not in any way meant to be limitative of the invention. The dimensions given are illustrative and would be suitable for a surgical drape for use on an adult patient. It will be understood that the stated dimensions may be varied, for example, for reasons of economy in materials or to provide smaller drapes for pediatric patients, without departing from the spirit and scope of the invention.

The assembly of drape 10 can best be understood by reference to FIG. 10 of the drawings. Main sheet 12, a 2.5 mil thick sheet of polyethylene measuring about 70 inches (177.8 cm.) long and 60 inches (152.4 cm.) wide is provided with fenestration 60 using either scissors or an appropriately size metal die. Closure means 62, preferably a "patch" of polyvinyl chloride, 2.5 mils thick, and measuring about 16 inches (40.6 cm.) long by 13 inches (33 cm.) wide, is over-all coated with a pressure sensitive adhesive and secured to main sheet 12 in the area shown generally by the stippling 85 in FIG. 10, so as to cover fenestration 60. Release sheet 65, somewhat larger in size than fenestration 60, is placed over and adhered to the adhesive which lies exposed within the perimeter of fenestration 60 on the lower surface of main sheet 12.

Bag means 32 comprises polyethylene and measures about 38 inches (96.5 cm.) long and 23 inches (58.4 cm.) wide. Retainer means 42 measures about 18 inches (45.7 cm.) long by 23 inches (58.4 cm.) wide. A plurality of holes are punched into the lower portion of the retainer means to allow liquids to pass therethrough. Retainer means 42 is inserted into bag means 32 so that open ends 34 of the bag means and 52 of the retainer means substantially coincide. The outer surface of retainer means 42 is then heat sealed (indicated by 80 in FIG. 9) to the inner surface of bag means 32 along a narrow zone of attachment running circumferentially and adjacent their open ends to provide the structure seen generally in the upper right hand portion of FIG. 10. Bag means 32 with retainer means 42 heat sealed thereto is secured with adhesive 82 to main sheet 22 along a line of attachment running from side to side of main sheet 12 and parallel to lower edge 15 thereof, said line of attachment being spaced downwardly about 5 inches (12.7 cm.) from the lowermost edge of fenestration 60.

Reinforcing panel 22, measuring about 34 inches (86.4 cm.) long and 20 inches (50.8 cm.) wide, is made from a 34 inch (86.4 cm.) long by 28 inch (71.1 cm.) wide piece of the aforementioned nonwoven/plastic laminate. Longitudinally extending side sections 8 inches (20.3 cm.) wide are folded in half (bringing plastic into contact with plastic) and glued with adhesive 70 (see FIG. 7) to provide flap portions 28 and 29 measuring 34 inches (86.4 cm.) long and 4 inches (10.2 cm.) wide. The reinforcing panel is then provided with opening 23 measuring 8-½ inches (21.6 cm.) long by 7-¼ inches (18.4 cm.) wide.

The reinforcing panel (but not flaps 28, 29) is coated with adhesive 84 and is secured, with its absorbent surface exposed, to main sheet 22 (and parts of closure means 62) so that opening 23 is centered over fenestration 60. As best seen in FIG. 9, a lower part [about 6 inches (15.2 cm.)] of reinforcing panel 22 is tucked into the open end of bag means 32, the lower surface of said reinforcing panel being secured to the inner surface of retainer means 42 with adhesive 84. The unattached bottom ends of flap portions 28, 29 are bent over upon themselves at an angle to form bent-over bottom ends 28a, 29a which are tucked inside bag means 32. The original lower surfaces of the bent-over bottom ends are then secured with a suitable adhesive to the lower surface of the front cover sheet of retainer means 42. This arrangement is generally the same as that shown in FIG. 15 in connection with the description hereinabove of drape 110 and serves the same purposes.

In surgical procedures involving the head, the patient's head is shaved clean in the operative area and the patient reclines on an operating table, the top of his head being relatively near the top edge of the table. An overhead instrument table is positioned over the area of the patient's chest, leaving the neck and head regions free for access. The overhead instrument table is suitably draped and the required surgical instruments are placed thereon.

The drape of FIG. 1 is placed on the patient as follows. The drape is held over the patient and protective sheet 65 is removed from the adhesive covering closure means 62. Closure means 62 is placed over the intended operative area and the drape is adhered to the patient's skin with adhesive 63. The top portion of the drape (that is, that portion thereof lying between the fenestration and top edge 14 of main sheet 12) is then extended upwardly and top edge 14 thereof is secured, for example, with towel clips, to the drape used to cover the overhead instrument table. The bottom portion of the drape (that is, that portion thereof lying generally between the fenestration and bottom edge 15 of main sheet 12) and bag means 32 are then left free to hang over the edge of the operating table. Flaps 28, 29 are then raised upwardly (with respect to their original position and the normal plane of main sheet 12) and, as this is done, the ends 28a, 29a of the flaps tend to open up the open end of bag means 32 and also retainer means 42 if such has been included in the drape. Any fluids (such as blood or irrigating fluids) encountered during surgery are then channeled downwardly by the now more or less upwardly extending flaps into bag means 32. If the earlier mentioned perforated retainer means has been placed within bag means 32, then the liquids will drain therethrough and be retained in the bag. Surgical sponges, disposable clamps and the like can be dropped into the open end of the bag means where they will be caught by retainer means 42 and stored until they can be counted at the end of the surgical procedure.

Drapes in accordance with the teachings of the present invention can be folded into a compact form, then packaged and sterilized. Drape 10 may be folded for packing by first fan folding bag means 32 so it overlies the upper surface of the main sheet and then fan folding the top and bottom portions of the main sheet toward its center. Once the drape has been folded to reduce its size in the longitudinal direction, it can then be folded transversely to provide a compactly folded drape suitable for packaging and sterilization.

What is claimed is:

1. A surgical drape comprising a main sheet of generally flexible drapable material, a liquid impervious bag means, and a pair of spaced apart strips of material; said main sheet comprising an upper surface, a lower surface, a bottom edge and a pair of opposed side edges; said bag means comprising a front cover sheet, a back cover sheet, an open end and a closed end and being secured to the upper surface of said main sheet; said strips of material being secured to the upper surface of said main sheet and having flap portions which are free of attachment to said main sheet, the respective bottom ends of said strips of material being located in the open end of said bag means, the lower surface of the bottom ends of said flap portions being secured to the lower surface of the front cover sheet of said bag means, whereby, when said drape is in use, said flap portions may be raised at an angle to the upper surface of said main sheet to provide means for channeling liquids into said bag for storage.

2. A surgical drape according to claim 1 wherein said main sheet comprises a material selected from the group consisting of nonwoven fabrics, scrim reinforced tissue, and plastic film.

3. A surgical drape according to claim 1 wherein the upper surface of said strips of material comprise a liquid absorbent nonwoven fabric and the lower surface comprises a liquid impervious plastic film.

4. A surgical drape according to claim 1 wherein said liquid impervious bag means comprises a plastic.

5. A surgical drape according to claim 1 wherein said liquid impervious bag means further comprises a liquid pervious retainer means secured to the inside of said bag means.

6. A surgical drape according to claim 5 wherein said liquid pervious retainer means comprises a perforated plastic film and is located relatively near the open end of said bag means.

7. A surgical drape according to claim 5 wherein said liquid pervious retainer means comprises a material selected from the group consisting of gauze and plastic netting.

8. A surgical drape according to claim 1 wherein said main sheet and said bag means comprise a plastic, said strips of material having an upper surface comprising a liquid absorbent nonwoven fabric and a lower surface comprising a liquid impervious plastic film, said bag means further including a liquid pervious retainer means which is located relatively near the open end of the bag means and which comprises a perforated plastic film.

9. A surgical drape comprising a main sheet of generally flexible drapable material, a reinforcing panel, and a liquid impervious bag means; said main sheet comprising an upper surface, a lower surface, a bottom edge and a pair of opposed side edges; said reinforcing panel being secured to the upper surface of said main sheet; said reinforcing panel comprising a top edge, a bottom edge, a pair of opposed side edges, and flap portions adjacent each of its side edges; said flap portions having respective bottom ends and being free of attachment to said main sheet; said bag means comprising a front cover sheet, a back cover sheet, an open end and a closed end; said bag means being secured to the upper surface of said main sheet along a line of attachment which is generally parallel to the bottom edge of said main sheet; the respective bottom ends of said flap portions being located in the open end of said bag means, the lower surface of the bottom ends of said flap portions being secured to the lower surface of the front cover sheet of said bag means, whereby, when said drape is in use, said flap portions may be raised at an angle to the upper surface of said main sheet to provide means for channeling liquids into said bag for storage.

10. A surgical drape according to claim 9 wherein said main sheet and said bag means comprise a plastic, said reinforcing panel having an upper surface comprising a liquid absorbent nonwoven fabric and a lower surface comprising a liquid impervious plastic film, said bag means further including a liquid pervious retainer means which is located relatively near the open end of the bag means.

11. A surgical drape according to claim 10 wherein said liquid pervious retainer means comprises a material selected from the group consisting of perforated plastic film, gauze, and plastic netting.

12. A surgical drape comprising a main sheet of generally flexible drapable material, a reinforcing panel, and a liquid impervious bag means; said main sheet comprising an upper surface, a lower surface, a bottom edge and a pair of opposed side edges; said main sheet having a fenestration located inwardly of the perimeter of said main sheet; said reinforcing panel being secured to the upper surface of said main sheet in the region adjacent said fenestration; said reinforcing panel comprising a top edge, a bottom edge, a pair of opposed side edges, and flap portions adjacent each of its side edges; said flap portions having respective bottom ends and being free of attachment to said main sheet; said bag means comprising a front cover sheet, a back cover sheet, an open end and a closed end; said bag means being secured to the upper surface of said main sheet along a line of attachment which is generally parallel to the bottom edge of said main sheet; the respective bottom ends of said flap portions being located in the open end of said bag means, the lower surface of the bottom ends of said flap portions being secured to the lower surface of the front cover sheet of said bag means, whereby, when said drape is in use, said flap portions may be raised at an angle to the upper surface of said main sheet to provide means for channeling liquids into said bag for storage.

13. A surgical drape according to claim 12 wherein said fenestration is covered with a closure means comprising a plastic film, said closure means having an adhesive on its lower surface within the area defined by the periphery of said fenestration.

14. A surgical drape according to claim 12 wherein said main sheet and said bag means comprise a plastic, said reinforcing panel having an upper surface comprising a liquid absorbent nonwoven fabric and a lower surface comprising a liquid impervious plastic film, said bag means further including a liquid purvious retainer means which is located relatively near the open end of the bag means.

15. A surgical drape according to claim 14 wherein said liquid pervious retainer means comprises a material selected from the group consisting of perforated plastic film, gauze, and plastic netting.

16. A surgical drape according to claim 14 wherein said liquid pervious retainer means comprises a perforated plastic film.

17. A surgical drape according to claim 16 wherein said adhesive on said closure means is protected, prior to use of the drape, by a removably adhered release covering.

18. A surgical drape according to claim 17 which is folded into a compact unit and packaged in a sterile condition.

* * * * *